(12) United States Patent
Makino et al.

(10) Patent No.: US 7,754,176 B2
(45) Date of Patent: Jul. 13, 2010

(54) SPHERICAL CALCIUM CARBONATE AND METHOD FOR PRODUCING THEREOF

(75) Inventors: Kenshiro Makino, Tokyo (JP); Kazuo Yamashita, Tokyo (JP)

(73) Assignee: Okutama Kogyo Co., Ltd. (JP)

( * ) Notice: Subject to any disclaimer, the term of this patent is extended or adjusted under 35 U.S.C. 154(b) by 832 days.

(21) Appl. No.: 10/547,000

(22) PCT Filed: Feb. 26, 2004

(86) PCT No.: PCT/JP2004/002268

§ 371 (c)(1),
(2), (4) Date: Aug. 26, 2005

(87) PCT Pub. No.: WO2004/076352

PCT Pub. Date: Sep. 10, 2004

(65) Prior Publication Data

US 2006/0165583 A1    Jul. 27, 2006

(30) Foreign Application Priority Data

Feb. 27, 2003    (JP) .............................. 2003-050311

(51) Int. Cl.
*C01F 11/18* (2006.01)
(52) U.S. Cl. ...................... 423/430; 423/432
(58) Field of Classification Search ........... 423/430, 423/432
See application file for complete search history.

(56) References Cited

U.S. PATENT DOCUMENTS 4,714,603 A * 12/1987 Vanderheiden .............. 423/432
6,312,659 B1 * 11/2001 Wise ........................ 423/430

FOREIGN PATENT DOCUMENTS

| EP | 0 179 597 A2 | 4/1986 |
|----|----|----|
| JP | 03-170327 | 7/1991 |
| JP | 4-4247 | 1/1992 |
| JP | 06-016417 | 1/1994 |
| JP | 07-033433 | 2/1995 |
| JP | 07-081931 | 3/1995 |
| JP | 10-059716 | 3/1998 |
| JP | 11-079740 | 3/1999 |
| JP | 2003-277050 | 10/2003 |

* cited by examiner

*Primary Examiner*—Stuart Hendrickson
(74) *Attorney, Agent, or Firm*—Bacon & Thomas, PLLC

(57) ABSTRACT

When spherical calcium carbonate is produced by blowing a carbon dioxide gas or a carbon dioxide-containing gas into an aqueous suspension containing calcium hydroxide to react them, after start of the reaction, an aqueous solution or suspension of a water-soluble phosphoric acid compound or a water-soluble salt thereof is added to the reaction mixture when carbonation ratio reaches 2 to 10%, and the reaction is further allowed to continue at a low gas blowing rate of 1.0 NL/minute or lower (step (a)). Subsequently, an aqueous suspension containing calcium hydroxide and an aqueous solution or suspension of a water-soluble phosphoric acid compound or a water-soluble salt thereof are added to the reaction mixture, and a carbon dioxide gas or a carbon dioxide-containing gas is introduced to allow to react and thereby produce spherical calcium carbonate having a mean particle diameter of 10 μm or larger. This production method is performed under high velocity revolution from the start of the reaction to the end of the step (a) This method provides calcite type spherical calcium carbonate showing high brightness and small friction coefficient, and having a shape comparatively close to a true sphere and a mean particle diameter of 10 μm or larger.

2 Claims, 1 Drawing Sheet

SPHERICAL CALCIUM CARBONATE AND METHOD FOR PRODUCING THEREOF

TECHNICAL FIELD

The present invention relates to calcite type spherical calcium carbonate and a method for producing the same.

BACKGROUND ART

Calcium carbonate is widely used as a filler or pigment for rubbers, plastics, paints, paper, cosmetics and so forth. Spherical calcium carbonate, in particular, has various superior characteristics such as filling property, dispersibility and lubricating property, and is used for mat coated paper in the field of papermaking and, as the other fields, cosmetics and so forth. As spherical calcium carbonate used for these uses, one having a small particle size (for example, several micrometers or smaller) has been conventionally desired in order to obtain a high degree of whiteness, gloss and dispersibility. However, in recent years, a pigment having a large particle size has come to be desired with multi-functionalization of the products for which calcium carbonate is used. For example, in the field of papermaking, a pigment having a mean particle diameter of 10 µm or larger is used for lusterless mat coated paper having a low degree of gloss. Moreover, also in cosmetics, a pigment having a specific feeling of touch, which cannot enter into pores, has comes to be used.

As the method of producing spherical calcium carbonate, various methods have been proposed so far, including a method of reacting an aqueous calcium chloride solution with an aqueous sodium carbonate solution, a method of reacting a water-soluble calcium salt with a carbonate salt in an aqueous solution in the presence of divalent cations other than calcium cations, a method of reacting calcium chloride and a hydrogencarbonate by using a phosphoric acid compound to produce vaterite type spherical calcium carbonate, and so forth. The method of using a phosphoric acid compound is described in, for example, Japanese Patent Unexamined Publication (KOKAI) No. 6-16417.

Further, methods of producing spherical calcium carbonate by using an additive when calcium carbonate is produced by introducing a carbon dioxide type gas into calcium hydroxide slurry have also been proposed. For example, Japanese Patent Publication (KOKOKU) No. 4-4247 describes a method of producing precipitated spherical calcite having a mean particle diameter of 2 to 10 µm by introducing carbon dioxide into calcium hydroxide slurry having a concentration of 15 to 20% which a predetermined amount of a polyphosphoric acid salt is added. Further, Japanese Patent Publication (KOKOKU) No. 7-33433 describes a method of producing calcite type spherical calcium carbonate having a mean particle diameter of 0.1 to 1.5 µm by mixing a reaction mixture in which calcium hydroxide slurry and carbon dioxide are reacted, and when the conductivity of the reaction mixture reaches a predetermined level, an oxyacid salt of phosphorus or a salt of a polymer or copolymer of unsaturated carboxylic acid is added and reacted, and a reaction mixture in which calcium hydroxide slurry and carbon dioxide are reacted until the conductivity of the reaction mixture reaches a predetermined level.

However, all the types of spherical calcium carbonate obtained by these conventional methods for producing spherical calcium carbonate have a mean particle diameter of less than 10 µm, and such spherical calcium carbonate having a comparatively large mean particle diameter as mentioned above cannot be produced. Although Japanese Patent Unexamined Publication No. 11-79740 proposes a method of producing spherical calcium carbonate secondary particles having a large specific surface area by spray-drying calcium carbonate obtained by introducing a carbon dioxide type gas into calcium hydroxide slurry, the spherical calcium carbonate obtained by this method consists of secondary particles having a mean particle diameter of 45 to 75 µm.

Therefore, an object of the present invention is to provide calcite type spherical calcium carbonate having a mean particle diameter of 10 µm or larger, showing high degree of whiteness and small friction coefficient as physical properties of fine particles, and having a shape comparatively close to a true sphere. Another object of the present invention is to provide utilization of such spherical calcium carbonate for various uses.

DISCLOSURE OF THE INVENTION

The inventors of the present invention assiduously conducted researches about reaction conditions, additives and addition conditions thereof for carbonation of calcium hydroxide by blowing a gas containing carbon dioxide into calcium hydroxide suspension. As a result, they found that if a water-soluble phosphoric acid compound or a salt thereof was added when the carbonation reached around 2 to 10% and reacted at a low gas blowing rate, and then calcium hydroxide suspension and a water-soluble phosphoric acid compound or a salt thereof were further added and reacted, the produced seed crystals could grow without forming aggregates of microparticles, and thus calcite type spherical calcium carbonate having a large mean particle diameter of which physical properties are not inferior to those of spherical calcium carbonate obtained by the conventional methods could be obtained, and thus they accomplished the present invention.

That is, the calcite type spherical calcium carbonate of the present invention is precipitated calcium carbonate produced by a reaction of an aqueous suspension containing calcium hydroxide and a carbon dioxide gas, and it is calcite type spherical calcium carbonate having a mean particle diameter of 10 to 20 µm.

Moreover, the method for producing calcite type spherical calcium carbonate of the present invention is a method for producing spherical calcium carbonate by blowing a carbon dioxide gas or a carbon dioxide-containing gas into an aqueous suspension containing calcium hydroxide to react them, which comprises the step (a) of, after start of the reaction, adding an aqueous solution or suspension of a water-soluble phosphoric acid or a water-soluble salt thereof to the reaction mixture when carbonation ratio reaches 2 to 10%, and further allowing to react at a low gas blowing rate, and the step (b) of, after the aforementioned step (a), adding an aqueous suspension containing calcium hydroxide and an aqueous solution or suspension of a water-soluble phosphoric acid or a water-soluble salt thereof (these are collectively and simply referred to as "phosphoric acid compound" hereinafter) to the reaction mixture, and introducing a carbon dioxide gas or a carbon dioxide-containing gas to allow to react and thereby produce spherical calcium carbonate.

In the present invention, when the gas blowing rate is represented in terms of amount of 100 volume % carbon dioxide gas per 1 kg of calcium hydroxide, a gas blowing rate of 1.0 NL or lower is referred to as "low gas blowing rate", and a gas blowing rate exceeding 1.0 NL is referred to as "high gas blowing rate".

In the present invention, around the time when the carbonation ratio reaches around 2 to 10%, which is the time point of adding the phosphoric acid compound, the descending conductivity shows the minimum value (minimum of primary descent) after the start of the reaction. If the reaction is continuously performed even after this time point, calcium carbonate is obtained as aggregates of microparticles, and generation of spherical calcium carbonate is inhibited. Therefore, by adding the phosphoric acid compound when the carbonation ratio reaches around 2 to 10%, preferably 4 to 6%, and performing the step (a) at a low gas blowing rate and under high velocity revolution, the formation of the aggregates of microparticles can be prevented.

The term "under high velocity revolution" means that the stirring velocity used for the reaction performed with stirring is a high velocity, and specifically, it refers to a velocity of 10 m/second or higher, preferably 12 m/or higher, as a revolving velocity of a stirrer bar provided in a reaction apparatus.

In the method for producing calcium carbonate of the present invention, it is preferred that when the carbonation ratio reaches 10 to 30% in the step (a), dilution water is further added to the reaction mixture, the reaction is completed at a high gas blowing rate, and then the step (b) is performed. By adding the dilution water, the produced particles can be dispersed in the system to suppress local reactions and promote production of truly spherical particles. Moreover, it can also prevent reduction of the reaction rate due to temperature rise.

The present invention also includes use of calcite type spherical calcium carbonate obtained by the aforementioned production method in cosmetics and coating solutions for papermaking.

BEST MODE FOR CARRYING OUT THE INVENTION

Figure 1:
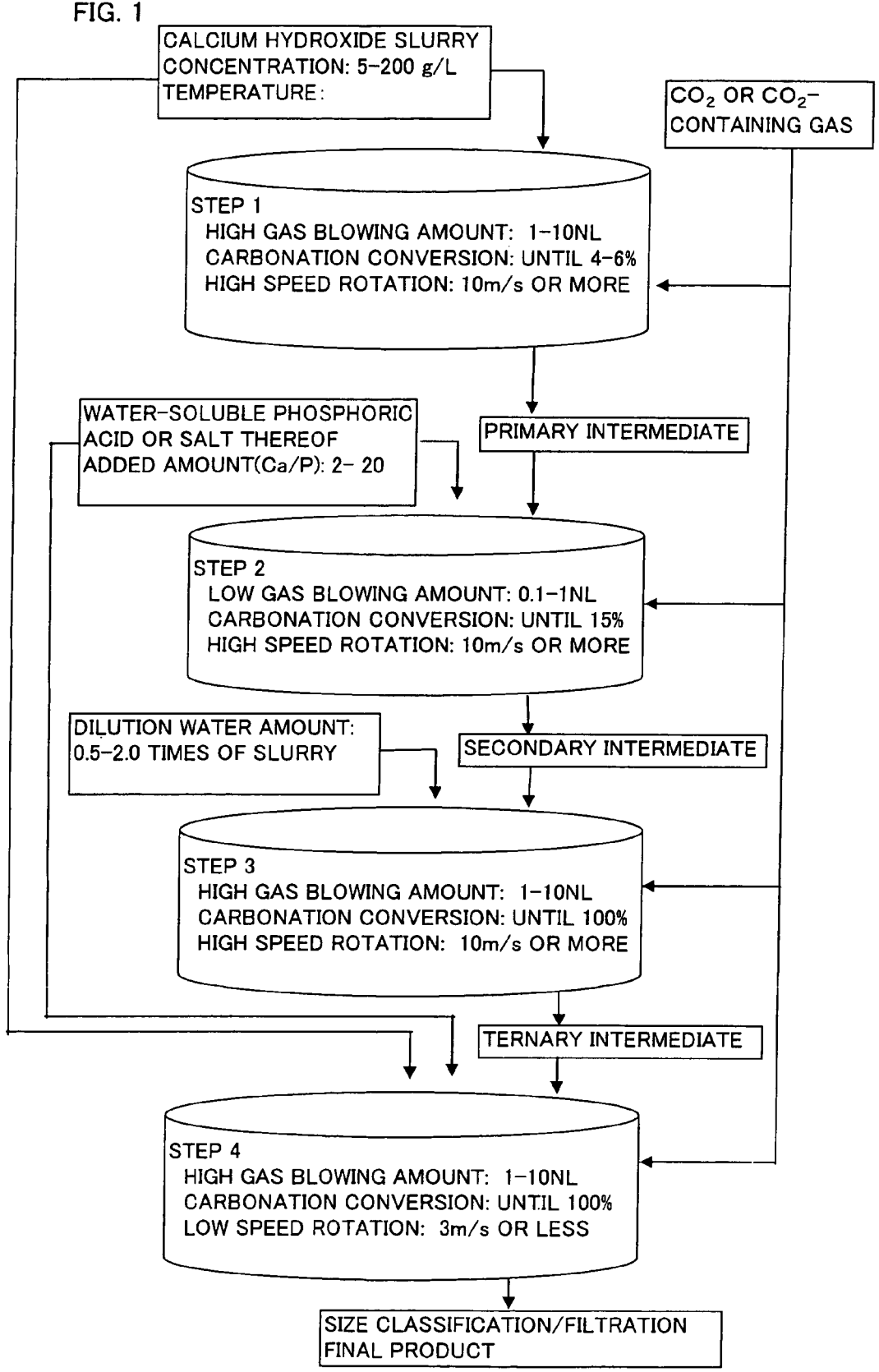
FIG. 1 shows one embodiment of the method for producing spherical calcium carbonate of the present invention.

Hereafter, the calcite type spherical calcium carbonate of the present invention and the method for producing the same will be explained in more detail.

1. Preparation of Raw Material

The aqueous suspension containing calcium hydroxide used in the production method of the present invention (henceforth also referred to as "calcium hydroxide slurry") can be prepared by mixing slaked lime with water, or wet-slaking quicklime (calcium oxide) with water. The wet slaking is preferably performed under the slaking conditions of a Ca concentration of 50 to 260 g/L, preferably 60 to 200 g/L, a temperature of 20 to 100° C., preferably 40 to 100° C., and an average dwell time in a slaker of 60 minutes or less, preferably 3 to 30 minutes, by using a wet type continuous slaker.

As water for the slaking, usual tap water, industrial water, groundwater, well water, or separated water obtained by the separation and dewater treatment of aqueous calcium carbonate slurry produced in the subsequent carbonation step or filtrate obtained by filtration treatment of the same.

2. Carbonation Reaction

By blowing a carbon dioxide gas or a carbon dioxide-containing gas into the calcium hydroxide slurry prepared as described above to cause the reaction, calcium carbonate is produced. This carbonation reaction comprises the step of producing seed crystals and the step of growing crystals, and it is preferably performed in a multistage scheme. Specifically, as shown in FIG. 1, for example, 1) first, after adjusting the calcium hydroxide concentration as required, a carbon dioxide gas or a carbon dioxide-containing gas is blown into the calcium hydroxide slurry, and the reaction is allowed to continue until the carbonation ratio of the reaction solution reaches around 2 to 10%, preferably 4 to 6% (Stage 1); 2) an aqueous solution or suspension of a water-soluble phosphoric acid compound or a water-soluble salt thereof is added, and the carbonation is further performed at a low gas blowing rate (Stage 2); 3) when the carbonation ratio reaches around 15% (10 to 30%), dilution water is added to the reaction mixture, and the reaction is allowed to continue at a high gas blowing rate to complete the reaction (Stage 3). These Stages 1 to 3 constitute the seed crystal producing step, and this step is performed under high velocity revolution. Then, 4) calcium hydroxide slurry and an aqueous solution or suspension of a water-soluble phosphoric acid compound or a water-soluble salt thereof is further added to the calcium carbonate obtained in the seed crystal producing step, and carbonation is further performed with blowing a carbon dioxide gas or a carbon dioxide-containing gas to grow crystals (Stage 4).

Each of the stages of the reaction can be performed under ordinary pressure or pressurization.

The reaction starting temperature is preferably 0 to 100° C., more preferably 5 to 50° C. Although the preferred range of the reaction temperature for each stage varies depending on the relation with the pressure conditions etc., it is determined within the range of 5 to 260° C. The particle formation velocity increases as the temperature and pressure as well as the stirring velocity become higher. However, increase of these factors may cause fluctuation of particle shape. Therefore, in order to obtain calcium carbonate of uniform particle shapes, the reaction is preferably performed at a temperature of 0 to 100° C.

The calcium hydroxide concentration in the reaction mixture for the carbonation reaction is preferably 50 to 200 g/L, more preferably about 50 to 150 g/L. If the amount of calcium carbonate becomes small, and the concentration becomes unduly low, the productivity decreases. On the other hand, if the amount is unduly large, and the concentration becomes unduly high, dispersibility of the water-soluble phosphoric acid salt or an aqueous solution or aqueous suspension thereof becomes unfavorable, and thus a local reaction becomes likely to occur. Therefore, uniform surface restoration by apatite can unfavorably no longer be obtained, and a mixture of calcium carbonate and apatite also unfavorably comes to be easily produced.

The pH value of the reaction mixture is preferably in the basic range during the stages of the reaction. Specifically, it is in the range of pH 8 to 13, preferably pH 9 to 11. If the pH value is unduly low, calcium phosphate other than apatite such as calcium hydrogenphosphate dihydrate ($CaHPO_4 \cdot 2H_2O$) is produced, and spherical calcium carbonate having uniform particle sizes or physical properties cannot be obtained. On the other hand, if the pH value is unduly high, pH of the suspension after the reaction becomes high, and it may unfavorably cause fluctuation of physical properties of the product or affect the product.

The blowing rate of the carbon dioxide gas or a carbon dioxide-containing gas is changed for each stage of the reaction. In the first stage (Stage 1), the blowing rate is set to be relatively high. Specifically, it should be in the range of 0.1 to 10 NL/minute in terms of amount of 100 volume % carbon dioxide gas per 1 kg of calcium hydroxide. With such a blowing rate, microparticles can be efficiently produced in an early stage of the reaction. After the water-soluble phosphoric acid compound or a water-soluble salt thereof is added (Stage 2), the gas blowing rate is lowered. Specifically, it is in the range of 0.1 to 1.0 NL/minute in terms of amount of 100 volume % carbon dioxide gas per 1 kg of calcium hydroxide.

The water-soluble phosphoric acid compound or a water-soluble salt thereof is added in order to form an apatite coating layer on the entire surface of calcium carbonate, and it is added at a time when the carbonation ratio becomes 2 to 10%, preferably 4 to 6%, in the reaction of Stage 1. If the time point of the addition is earlier than the above, for example, if it is added at the same time as the start of the reaction, or added when the carbonation ratio exceeds 10%, calcium carbonate having a large mean particle diameter cannot be produced in the both cases. Examples of the water-soluble phosphoric acid compound include, for example, orthophosphoric acid, metaphosphoric acid, pyrophosphoric acid, polyphosphoric acid and so forth, and examples of the water-soluble salt thereof include, for example, $NH_4H_2PO_4$, $(NH_4)_2HPO_4$, $(NH_4)_3PO_4$, $NaH_2PO_4$, $Na_2HPO_4$, $Na_3PO_4$, $KH_2PO_4$, $K_2HPO_4$, $K_3PO_4$ and so forth. These can be used as a simple substance or a combination of two or more kinds of them.

These water-soluble phosphoric acid compounds or water-soluble salts thereof are preferably added as an aqueous solution or an aqueous suspension. It is important that, as for the addition amount, they should be added in a sufficient amount or suitable concentration for forming an apatite coating layer on the entire surface of calcium carbonate. Specifically, it is selected so that the ratio of Ca/P (molar ratio) of the precipitated calcium carbonate and the water-soluble phosphoric acid compound should be in the range of 2 to 20, preferably 10 to 20. If this ratio is too small, a mixture of precipitated calcium carbonate and apatite is produced. On the other hand, if the ratio is too large, the formation of apatite coating layer on the entire surface of the precipitated calcium carbonate unfavorably becomes insufficient.

After the water-soluble phosphoric acid compound or a water-soluble salt thereof is added, the reaction is performed under a low gas blowing rate condition of the carbon dioxide gas or carbon dioxide-containing gas with high velocity revolution as described above (reaction of Stage 2). Specifically, the reaction is performed at a velocity of 10 m/second or higher, preferably 12 m/or higher, as a revolving velocity of a stirrer bar. By performing the seed crystal producing step with high velocity revolution and controlling the gas volume in each of the stages as described above, aggregation of microparticles can be suppressed, and crystals in a true spherical shape can be grown in the subsequent stage.

Although it is also possible to terminate the reaction (to make the carbonation ratio 100%) under these conditions of Stage 2, it is preferable to add dilution water when the carbonation ratio becomes around 15% (10 to 30%) in Stage 2, and then the reaction of Stage 3 is performed. In Stage 3, a high gas blowing rate condition is used, and the reaction is performed with high velocity revolution. Specifically, the gas blowing rate is the same as or higher than that used in Stage 1, and the revolution velocity may be the same as that used in Stage 1.

By adding dilution water before the reaction terminates as described above, reduction of the reaction rate due to temperature rise can be prevented, and at the same time, the produced particles can be dispersed in the system. Then, local reactions can be suppressed. Although the addition amount of the dilution water is not particularly limited, it is preferably added so that the concentration of the reaction mixture should become about ½, and it is about 0.5 to 2.0 times, preferably 0.8 to 1.3 times, the amount (volume) of the aqueous calcium hydroxide slurry charged before the start of the reaction.

3. Crystal Growing Step

After completion of the aforementioned carbonation steps 1) to 3) for producing seed crystals, calcium hydroxide slurry and an aqueous solution of a water-soluble phosphoric acid compound or a water-soluble salt thereof are further added, and the carbonation is continued at a temperature of 0 to 100° C. under ordinary pressure or pressurization to grow crystals.

As the calcium hydroxide slurry used in the crystal growing step, the calcium hydroxide slurry prepared in the seed crystal producing step can be continuously used. Further, the concentration of the calcium hydroxide slurry and addition amount of the water-soluble phosphoric acid compound or a water-soluble salt thereof used in this carbonation step may be the same as those used in the a seed crystal producing step. However, in this stage, a lower stirring velocity is preferred. If the velocity is increased, the production rate increases, and the surfaces of the spherical particles unfavorably tend to be distorted. Specifically, the velocity is preferably about one severalth of that used in the crystal producing step in terms of the peripheral speed of the stirring bar.

After the carbonation, the reaction slurry is filtered through a sieve such as vibrating sieve to obtain the spherical calcium carbonate of the present invention. In this case, it is preferable to subject the slurry to classification using a liquid cyclone prior to the filtration through a sieve. By performing the classification using a liquid cyclone, clogging of the sieve and contamination due to microparticles can be prevented.

4. Use

The thus produced spherical calcium carbonate of the present invention is calcite type calcium carbonate having a mean particle diameter of 10 µm or larger, and can be used for known purposes of calcium carbonate, for example, as a pigment, filler, cosmetic and so forth, and in particular, purposes requiring calcium carbonate having a comparatively large particle size. Specifically, it can be preferably used for papermaking, especially as a coating pigment for mat coated paper, cosmetics, filler of plastics, films, rubbers and so forth. The spherical calcium carbonate of the present invention is bulky because it consists of macroparticles, and shows superior whiteness.

EXAMPLES

Hereafter, the present invention will be explained in more detail with reference to the following examples. However, the present invention is no way limited by these examples.

In the following examples, the blowing rates of the carbon dioxide or carbon dioxide-containing gas are represented in terms of amounts of 100% carbon dioxide gas at 20° C. Further, the particle diameters of calcium carbonate (median diameters (µm)) are values measured by means of a laser diffraction/scattering type particle size distribution analyzer (LA-920, produced by Horiba, Ltd.).

1. Preparation of Spherical Calcium Carbonate

Example 1

86 kg of quicklime was put into 1000 L of water (conductivity: 0.05 mS/cm) to obtain aqueous calcium hydroxide slurry (slaked lime milk) having a concentration of 105 g/L. Subsequently, after this slurry was adjusted to a concentration of 100 g/L and 20° C., 150 L of the slurry was charged into a semi-batch type reactor, and a gas having a carbon dioxide concentration of 30 volume % was blowed into the slurry at a rate of 3 NL/minute in terms of the amount of 100 volume % carbon dioxide per 1 kg of calcium hydroxide with stirring at a peripheral speed of 13 m/second. When the carbonation ratio of the reaction mixture reached 4% or around 4%, the reaction was primarily terminated to obtain a primary reaction intermediate (Stage 1).

Sodium hexametaphosphate was added in an amount of 1.5 parts by weight with respect to 100 parts by weight of calcium hydroxide in the primary reaction intermediate as an aqueous solution having a solid content concentration of 2% to the aforementioned primary reaction intermediate and mixed, and then a gas having a carbon dioxide concentration of 30 volume % was blown into the reaction intermediate at a rate of 0.3 NL/minute in terms of amount of 100 volume % carbon dioxide per 1 kg of calcium hydroxide with stirring at a peripheral speed of 13 m/second. When the carbonation ratio reached 15% or around 15%, the reaction was secondarily terminated to obtain a secondary reaction intermediate (Stage 2).

After 150 L of water at 20° C. was added to the secondary reaction intermediate to dilute the secondary reaction intermediate, a gas having a carbon dioxide concentration of 80 volume % was blown into the reaction intermediate at a rate of 3.6 NL/minute in terms of amount of 100 volume % carbon dioxide per 1 kg of calcium hydroxide with stirring at a peripheral speed of 13 m/second, and the reaction was terminated to obtain a tertiary intermediate (Stage 3).

150 L of the aforementioned tertiary reaction intermediate and 150 L of aqueous calcium hydroxide slurry (concentration: 50 g/L), to which 1.0 part by weight with respect to 100 parts by weight of calcium hydroxide in the reaction intermediate of sodium hexametaphosphate was added as an aqueous solution having a solid content concentration of 2%, were charged into a semi-batch type reactor, and adjusted to 20° C. Then, a gas having a carbon dioxide concentration of 30 volume % was blown into the mixture at a rate of 3 NL/minute in terms of amount of 100 volume % carbon dioxide per 1 kg of calcium hydroxide with stirring at a peripheral speed of 2.6 m/second to complete the reaction (Stage 4).

The thus obtained aqueous slurry of spherical calcium carbonate was filtered and dehydrated by using a filter press to obtain a dehydrated cake having a solid content concentration of 40% by weight, and the cake was dried in a dryer and then subjected to a grinding treatment to obtain powder. This powder consisted of spherical particles having a mean particle diameter of 13.0 μm, and it was confirmed to be calcite on the basis of the result of X-ray diffraction analysis.

Example 2

A tertiary reaction intermediate was obtained in the same manner as in Example 1. Except that 210 L of this tertiary reaction intermediate and 90 L of aqueous calcium hydroxide slurry (concentration: 50 g/L), to which sodium hexametaphosphate in an amount of 1.0 part by weight with respect to 100 parts by weight of calcium hydroxide in the slurry was added as an aqueous solution having a solid content concentration of 2%, were charged into a semi-batch type reactor, calcium carbonate was produced in the same manner as that used in Example 1.

The thus obtained spherical calcium carbonate consisted of spherical particles having a mean particle diameter of 11.5 μm, and it was confirmed to be calcite on the basis of the result of X-ray diffraction analysis.

Example 3

A tertiary reaction intermediate was obtained in the same manner as in Example 1. Except that 90 L of this tertiary reaction intermediate and 210 L of aqueous calcium hydroxide slurry (concentration: 50 g/L), to which sodium hexametaphosphate in an amount of 1.0 part by weight with respect to 100 parts by weight of calcium hydroxide in the slurry was added as an aqueous solution having a solid content concentration of 2%, were charged into a semi-batch type reactor, calcium carbonate was produced in the same manner as in Example 1.

The thus obtained spherical calcium carbonate consisted of spherical particles having a mean particle diameter of 16.3 μm, and it was confirmed to be calcite on the basis of the result of X-ray diffraction analysis.

Comparative Example 1

(The Crystal Growing Step was not Used)

A tertiary reaction intermediate was obtained in the same manner as in Example 1, and when the tertiary reaction intermediate was obtained, the reaction was terminated, and the produced spherical calcium carbonate was collected.

The thus obtained spherical calcium carbonate consisted of spherical particles having a mean particle diameter of 7.8 μm, and it was confirmed to be calcite on the basis of the result of X-ray diffraction analysis.

Comparative Example 2

(The Phosphoric Acid Compound was Added at Stage 1)

The same calcium hydroxide aqueous slurry as that used in Example 1 (concentration: 100 g/L, 20° C.) in a volume of 150 L was charged into a semi-batch type reactor, sodium hexametaphosphate in an amount of 1.5 parts by weight with respect to 100 parts by weight of calcium hydroxide in the slurry was added as an aqueous solution having a solid content concentration of 2% and mixed, and then a gas having a carbon dioxide concentration of 30 volume % was blown into the slurry at a rate of 0.3 NL/minute in terms of amount of 100 volume % carbon dioxide per 1 kg of calcium hydroxide with stirring at a peripheral speed of 13 m/second. When the carbonation ratio reached 15% or around 15%, the reaction was terminated to obtain a primary reaction intermediate.

Water at 20° C. was added in a volume of 150 L to the reactor to dilute the primary reaction intermediate, then a gas having a carbon dioxide concentration of 80 volume % was bubbled into the reaction intermediate at a rate of 3.6 NL/minute in terms of amount of 100 volume % carbon dioxide per 1 kg of calcium hydroxide with stirring at a peripheral speed of 13 m/second to terminate the reaction, and the produced spherical calcium carbonated was collected.

The thus obtained spherical calcium carbonate consisted of spherical particles having a mean particle diameter of 4.7 μm, and it was confirmed to be calcite on the basis of the result of X-ray diffraction analysis.

Comparative Example 3

(The Phosphoric Acid Compound was Added when the Carbonation Ratio Reached 12%)

The reaction was performed in the same manner as in Example 1, Stage 1, but the reaction was allowed to continue until the carbonation ratio reached 12%, and then the reaction was primarily terminated to obtain a primary reaction intermediate. Subsequently, the reaction was performed in the same manner as in Example 1, Stages 2 and 3, and the produced spherical calcium carbonate was collected.

It was confirmed that the thus obtained calcium carbonate consisted of aggregates of microparticles having a mean particle diameter of 5.6 µm.

Comparative Example 4

(Stage 2 after Addition of the Phosphoric Acid Compound was Performed Under a High Gas Blowing Rate Condition)

The reaction was performed in the same manner as in Example 1, Stages 1 to 3, except that the gas blowing rate used in Example 1, Stage 2 was changed to 1.7 NL/minute as a high gas blowing rate condition, and the produced spherical calcium carbonate was collected.

It was confirmed that the thus obtained calcium carbonate consisted of aggregates of microparticles having a mean particle diameter of 4.8 µm.

Comparative Example 5

(Stage 2 after Addition of the Phosphoric Acid Compound Addition was Performed Under a Low Velocity Revolution Condition)

The reaction was performed in the same manner as in Example 1, Stages 1 to 3, except that the revolution number of the stirrer bar in Example 1, Stage 2 was changed to 7.8 m/second as a low revolution condition, and the produced spherical calcium carbonate was collected.

It was confirmed that the thus obtained calcium carbonate consisted of a mixture of aggregates of microparticles and spherical particles having a mean particle diameter of 4.7 µm.

The reaction conditions of Example 1 and Comparative Examples 1 to 5 and the mean particle diameters of the calcium carbonate obtained therein are summarized in Table 1.

As seen from the results shown in Table 1, when the crystal growing step was not used, calcium carbonate having a mean particle diameter of 10 µm or larger could not be obtained. As also seen from comparison of the results of Comparative Example 1 and Comparative Examples 2 to 5, when the phosphoric acid compound was added at an early stage, the phosphoric acid compound was added at a carbonation ratio of 12%, or the reaction after the addition of the phosphoric acid compound was performed under a high gas blowing rate or low velocity revolution condition in the crystal producing step, large seed crystals could not be produced in all the cases.

2. Evaluation of Calcium Carbonate

Dynamic friction coefficient (µm) of the calcium carbonate powders obtained in Examples 1 to 3 and Comparative Example 1 was measured as follows according to J. TAPPI Paper Pulp Test Method No. 30-79. A double stick tape was adhered on a sample stand, a predetermined amount (18 to 20 g/m$^2$) of the powder was put on the surface of the tape, and dynamic friction coefficient was measured by using Strograph R produced by TOYO SEIKI SEISAKU-SHO, LTD. The results are shown in Table 2.

3. Preparation of Coating Solution for Papermaking and Production of Coated Paper Dried powders of calcium carbonate obtained in Examples 1 to 3 and Comparative Example 1 were each mixed with water and a dispersing agent (1% of $CaCO_3$) so that the solid content concentration should become about 68% to prepare calcium carbonate slurry.

Each calcium carbonate slurry prepared as described above was coated as a coating solution on one side of fine quality paper (basis weight: 81 g/m$^2$) in an amount of about 22 m$^2$/g by using a lot bar for manual coating and dried to produce coated paper.

The physical properties of the coated paper were measured by the following methods. The results are shown in Table 2.

Gloss of white paper: measured according to JIS P8142

Ink acceptability: measured according to JAPAN TAPPI No. 46

TABLE 1

| | Seed crystal producing step | | | Crystal growing step | Mean |
| --- | --- | --- | --- | --- | --- |
| | Stage 1<br>Gas volume (NL)<br>Peripheral speed (m/s) | Stage 2<br>Gas volume (NL)<br>Peripheral speed (m/s) | Stage 3<br>Gas volume (NL)<br>Peripheral speed (m/s) | Stage 4<br>Gas volume (NL)<br>Peripheral speed (m/s) | particle<br>diameter<br>(µm) |
| Example 1 | 3<br>13 | 0.3<br>13 | 3.6<br>13 | 3<br>2.6 | 13.0 |
| Comparative Example 1 | 3<br>13 | 0.3<br>13 | 3.6<br>13 | Not used | 7.8 |
| Comparative Example 2 | Phosphoric acid compound was added at an early stage<br>0.3<br>13 | | 3.6<br>13 | Not used | 4.7 |
| Comparative Example 3 | Same as Example 1 | Phosphoric acid compound was added at carbonation ratio of 12% | 3.6<br>13 | Not used | 5.6 |
| Comparative Example 4 | " | 1.7 NL<br>13 m/s | 3.6<br>13 | Not used | 4.8 |
| Comparative Example 5 | " | 0.3 NL<br>7.8 m/s | 3.6<br>13 | Not used | 4.7 |

TABLE 2

|  | Example 1 | Example 2 | Example 3 | Comparative Example 1 |
|---|---|---|---|---|
| LA-920 (μm) | 13.0 | 11.5 | 16.3 | 7.8 |
| Gloss of white paper (%) | 6.1 | 6.4 | 5.8 | 6.5 |
| Ink acceptability (%) | 15.2 | 14.2 | 15.3 | 14.2 |

As seen from the results shown in Table 2, spherical calcium carbonate having a large particle size and showing superior gloss of white paper could be obtained according to the present invention. The coated paper using this calcium carbonate had brightness comparable to that of coated paper using conventional spherical calcium carbonate having a small particle size, and also showed good ink acceptability.

INDUSTRIAL APPLICABILITY

According to the present invention, spherical calcium carbonate of calcite type, which is a stable crystalline form, having a mean particle diameter of 10 μm or larger can be provided. Further, according to the present invention, spherical particles having a mean particle diameter of 20 μm at most or 11 μm at least can be selectively produced.

Furthermore, if the calcite type spherical calcium carbonate of the present invention is used as a coating pigment, it can provide paper materials showing a comparatively high brightness and low gloss of white paper, which sufficiently fulfill the characteristics of mat coated paper. Moreover, because the calcite type spherical calcium carbonate of the present invention has a dynamic friction coefficient (μm) almost comparable to that of the same material having a small mean particle diameter, and has a particle size that does not allow the particles to enter into pores etc., it is effective as a cosmetic affecting foreign body sensation such as feeling of touch.

The invention claimed is:

1. Non-aggregated calcium carbonate spheres produced by introducing a carbon dioxide gas or a carbon dioxide-containing gas into an aqueous suspension containing calcium hydroxide to react them, wherein a water-soluble phosphoric acid compound is added only when the carbonization ratio has reached 2-10%, wherein the gas is introduced at a rate of no greater than 1.0 NL/minute, as 100 volume % carbon dioxide and wherein the suspension is stirred with a stirrer peripheral speed of at least 10 m/sec, the spheres having a mean particle diameter of at least 11 μm.

2. The calcium carbonate spheres according to claim 1, wherein the spheres are calcite crystal spheres.

* * * * *